(12) United States Patent
Chu et al.

(10) Patent No.: US 7,303,552 B1
(45) Date of Patent: Dec. 4, 2007

(54) SPLIT VALVE FOR PEEL-AWAY SHEATH

(75) Inventors: Michael S. H. Chu, Brookline, MA (US); Yem Chin, Burlington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 869 days.

(21) Appl. No.: 09/430,050

(22) Filed: Oct. 29, 1999

(51) Int. Cl.
*A61M 5/00* (2006.01)
(52) U.S. Cl. .................................... 604/263
(58) Field of Classification Search ............... 604/263, 604/164.01–164.09, 160, 161, 165.01–165.03, 604/166.01, 167.01, 264, 905
See application file for complete search history.

(56) References Cited

U.S. PATENT DOCUMENTS

| 4,247,076 A | 1/1981 | Larkin .......................... 251/7 |
| 4,429,852 A | 2/1984 | Tersteegen et al. ............ 251/9 |
| 5,125,904 A * | 6/1992 | Lee ............................. 604/164 |
| 5,250,033 A | 10/1993 | Evans et al. ................. 604/160 |
| 5,312,355 A | 5/1994 | Lee ............................. 604/160 |
| 5,397,310 A | 3/1995 | Chu et al. .................... 604/158 |
| 5,397,311 A | 3/1995 | Walker et al. .............. 604/160 |
| 5,441,504 A | 8/1995 | Pohndorf et al. ........... 606/129 |
| 5,549,657 A | 8/1996 | Stern et al. ................. 604/283 |
| 5,613,953 A | 3/1997 | Pohndorf .................... 604/165 |
| 6,083,207 A * | 7/2000 | Heck .......................... 604/256 |

FOREIGN PATENT DOCUMENTS

EP 0 948 970 A2 10/1999
WO WO 93/06878 A1 4/1993

OTHER PUBLICATIONS

"Banana Peel™ Sheath" Instruction Sheet, undated, 1 page.
"Banana Peel™ Sheath" Instruction Sheet, undated, 1 page, no date available.

* cited by examiner

*Primary Examiner*—Ann Y. Lam
(74) *Attorney, Agent, or Firm*—Crompton, Seager & Tufte, LLC (57) ABSTRACT

A breakaway valve body for a peel-away introducer sheath. The valve body can be used in conjunction with a distally coupled peel-away introducer sheath and a proximally coupled flexible valve sleeve for restricting fluid flow from the introducer sheath when the valve body compresses the valve sleeve to a closed position. The valve can include a body scored or weakened to break along a predefined path in response to applied force. The valve preferably includes a first member and a second member movable relative to each other and having a pinch member therebetween for constricting a flexible valve sleeve placed between the first and second members. In one valve, the first and second members are pivotally disposed on hinges to allow the members to open and close about an inserted flexible valve sleeve and to pinch the sleeve with a pinch member. The valve preferably includes a proximal region of valve sleeve extending proximally past the valve pinch member to allow insertion of a catheter distal end into the valve sleeve proximal end while the more distal valve sleeve region is constricted in a closed position. The valve allows insertion of a catheter into the introducer sheath with minimal blood loss. The valve allows easy removal of the sheath from an inserted catheter by snapping the valve and pulling the halves apart, thereby tearing the peel-away sheath away from the catheter.

15 Claims, 6 Drawing Sheets

SPLIT VALVE FOR PEEL-AWAY SHEATH

FIELD OF THE INVENTION

The present invention is generally related to medical devices. More specifically, the present invention is related to introducer sheaths for introducing catheters into the body. The present invention includes a breakaway split valve for restricting fluid flow from a peel-away sheath extending from the body.

BACKGROUND OF THE INVENTION

Introducer sheaths are well-known devices which can be used to introduce catheters through body conduits into the human body. Introducer sheaths are often used to facilitate the insertion of catheters into body vessels where placement of the catheter without an introducer sheath may present difficulty. Sheaths are useful where the tract to be traversed is tortuous or obstructed. Introducer sheaths are commonly used in applications where backflow of bodily fluids through the introducer sheath does not present a problem. Typical applications do not include insertion of the sheath into blood vessels, where backflow of blood through the sheath can present a problem. For this reason, introducer sheaths have seen limited use in vascular applications.

When catheters are inserted into the vasculature, such as into an artery near the groin as in Percutaneous Transluminal Angioplasty (PTCA) procedures, there is substantial blood pressure within the artery. The catheter is typically sealed at the point of insertion to prevent outflow around the inserted catheter. Any internal catheter back-flow is typically prevented using proximal end manifolds having attached Luer fittings, Tuohy-Borst closures, stop cocks, and other reversibly closeable devices.

Introducer sheaths are often introduced over a previously inserted guide wire. As sheaths are sometimes very flexible and the target pathway very tortuous, a coaxially tapered dilator is often used in conjunction with the introducer sheath for the purpose of advancing the sheath to the target site. The dilator can be withdrawn after the introducer sheath is in position. After a catheter has been advanced through the introducer sheath, the sheath has usually served its purpose and can be removed. If the sheath were not a peel-away sheath, removal over the inserted catheter and proximal catheter manifold could prove difficult. A peel-away sheath provides a means for removing the sheath by peeling it away from the catheter it surrounds, typically by tearing the sheath apart in halves, in opposite directions transversely away from the catheter.

In order to peel away the sheath, any sheath proximal end fixture must typically be peeled away or broken away as well. In applications where backflow is not a major problem, this is not a major issue as the sheath proximal end can be open and the proximal fixture, if any, is minimal. In vascular applications, where blood pressure makes backflow through the sheath a problem, the proximal fixture should include a valve that is able both to substantially restrict blood backflow and to admit an inserted catheter.

What would be desirable is a valve for use with peel-away introducer sheaths where the valve can be open, shut, and broken apart for removal from the inserted catheter. What would be advantageous is a breakaway valve for an introducer sheath which also minimizes backflow during introduction of a catheter through the valve.

SUMMARY OF THE INVENTION

The present invention includes a breakaway valve for use with a peel-away introducer sheath. The valve can include a breakaway valve body having a distal coupling for sealingly mating to a distal introducer sheath and a movable pinch member for compressing an inserted flexible tubular valve sleeve. In a preferred embodiment, the valve body includes two opposed members having an open position and a closed position about the valve sleeve. In a preferred embodiment, the valve sleeve includes a free end having a proximal region proximally past the pinch member for allowing entry of a catheter distal end while the valve body is in the closed position.

One valve includes a breakaway distal portion having a lumen therethrough for receiving the introducer sheath proximal region and a proximal portion including two opposed body members movable relative to each other and having facing concave surfaces for receiving a flexible valve sleeve therebetween. The valve body members can have an open position and a closed position, wherein the valve body members move apart relative to each other to reach the open position and move together to reach the closed position. The valve sleeve restricts or prevents fluid backflow through the constricted valve sleeve lumen in the closed position, and allows passage of an inserted catheter while in the open position.

In valve bodies having two opposed members, the members can be pivotally mounted to each other on a hinge substantially parallel to the longitudinal axis of the introducer sheath lumen. In other embodiments, the two valve body members can each be mounted on hinges lying in a plane substantially transverse to the introducer sheath lumen longitudinal axis. In one embodiment, one valve body member includes a concave inner surface for receiving a flexible valve sleeve, while the other member includes a hinged arm carrying a valve sleeve pinch member, the arm held in position with a ratcheting free end fixable at one of several notches on the valve body.

In one embodiment, the pinch member is disposed midway through the valve body, and the valve body includes a proximal port, even when closed, for admitting a catheter distal end into the closed valve body and into the free, open end of a flexible valve sleeve. In another embodiment, the pinch member is disposed near the proximal end of the valve body, and the valve sleeve includes a portion extending proximally from the valve body. Some embodiments include a recess or guide wire lumen through the pinch member or members, even when closed, to allow for the presence of a guide wire without clamping down on the guide wire surface when the valve body is in the closed position.

In use, a guide wire can be inserted into the vasculature of a patient, followed by an introducer sheath over the guide wire. The introducer sheath can be advanced with the aid of a dilator in some procedures. After placement of the sheath is complete, the dilator can be retracted, leaving the sheath disposed over the guide wire. The sheath typically will have a proximal portion extending from the patient, with the proximal breakaway valve disposed at the proximal end of the sheath.

The valve can then be in the closed position, having the guide wire extending through the valve and out the proximal end of the valve. The guide wire, enclosed in the constricted valve sleeve, lies within a guide wire lumen or recess in some valves which allows for tight closure of the valve body. In other valves lacking a special recess, the valve body can still tightly compress the flexible valve sleeve together and about the guide wire, greatly restricting any blood backflow.

When introduction of a catheter is called for, the catheter distal end can be inserted into the proximal end of the flexible valve sleeve proximal of the closed pinch point. When the valve body is next opened, the catheter distal end substantially occludes the inside of the valve sleeve, substantially restricting blood backflow, even when the valve sleeve is open. The catheter can be advanced through the introducer sheath to the target site.

With the catheter in position, the valve body can be fully opened, if not open already, with the two movable valve body halves disposed well apart. The valve body can be broken along the weakened areas to break the valve body apart, typically in half. The body halves can be pulled apart. As the body halves are typically bonded to the introducer sheath, the sheath is torn in half as well, peeling the sheath away from the inserted catheter. The introducer sheath can be withdrawn from the patient as it is peeled away, and the sheath disposed of.

DETAILED DESCRIPTION OF THE INVENTION

Figure 1:
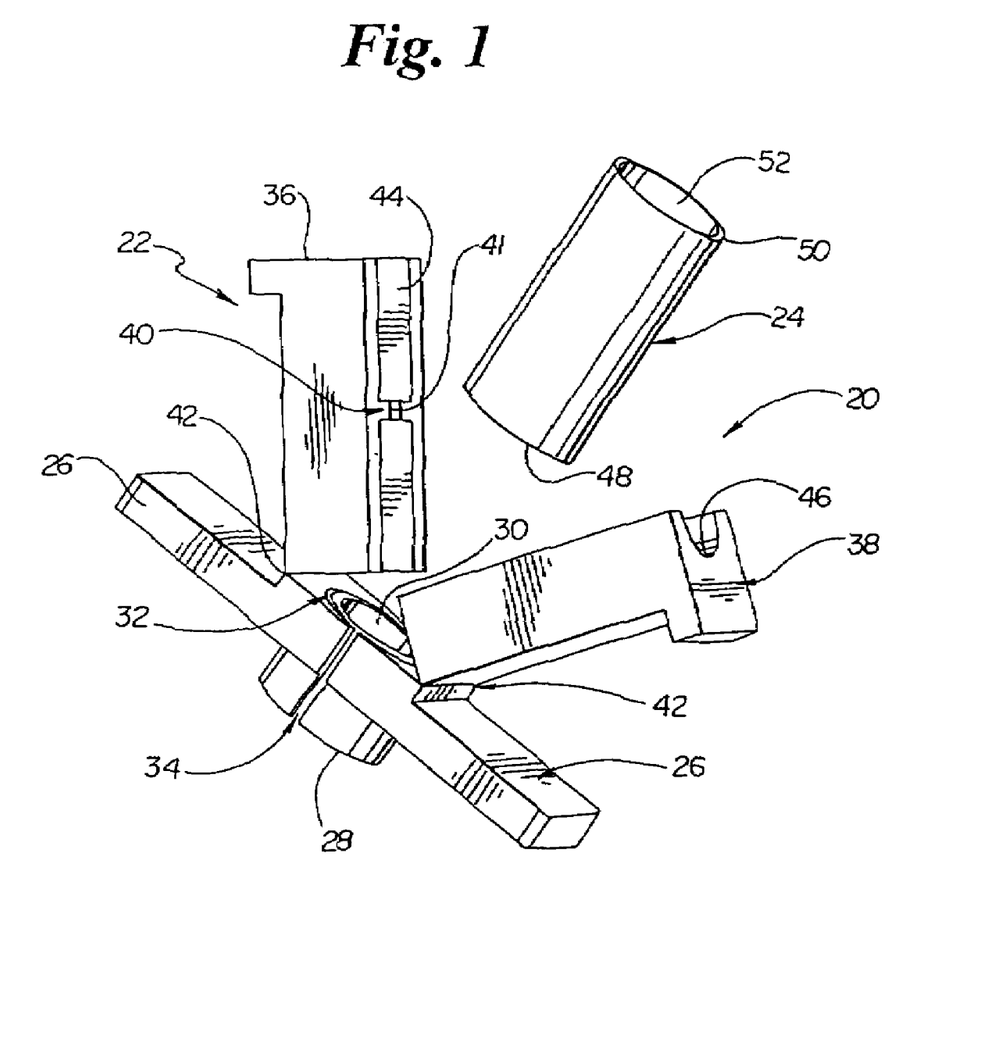
FIG. 1 is an exploded, perspective view of a split valve for a peel-away sheath having a mid-range pinch point shown in an open position, together with a proximal valve sleeve.

FIG. 1 illustrates a split valve 20 including a valve body 22 and a valve sleeve 24. Valve 20 includes a distal end 28, a pair of graspable handles or ears 26, a valve sleeve seat 32, and a lumen 30 therethrough. Valve body 22 includes a first moveable member 36, a second moveable member 38, a laterally-oriented pinch member 40, and a pair of snap grooves 34 (only one being visible in FIG. 1). Valve 20 is shown in an open position, having been opened along a pair of hinges 42 lying in a plane substantially transverse to the longitudinal axis of lumen 30. A tubular valve body lumen is formed when the valve body is in a closed position, the lumen being formed by a first concave portion 44 in first body member 36 and a second concave portion 46 in second body member 38.

Valve sleeve 24 has a distal end 48, a proximal region 50, and lumen 52 therethrough. Valve sleeve 24 is adapted to be received between valve body members 36 and 38. Valve body 22 is preferably formed of a rigid polymeric material such as polyethylene. Valve sleeve 52 is preferably formed of a flexible, polymeric material such as silicone, latex, or polyurethane. The material should be elastic so as to spring back to an open shape after a constricting force is removed. Snap groove 34 can be irreversibly separable. In irreversibly splitable embodiments, the groove can be a weakened longitudinal strip of preferential breakage along its length. The groove or other structure will break along a defined path when the user applies sufficient external force to snap the valve in half.

Valve sleeve seat 32 is adapted to receive valve sleeve distal end 48. When valve sleeve distal end 48 abuts valve sleeve seat 32, first and second body members 36 and 38 can be pivoted about hinges 42 to close upon inserted valve sleeve 24. When in the closed position, valve sleeve 24 will be pinched by pinch member 40 and its opposing counterpart (not visible in FIG. 1), thereby greatly constricting valve sleeve lumen 52. In the embodiment illustrated in FIG. 1, pinch member 40 includes a small recess 41 to limit the amount of valve sleeve constriction to allow a guide wire to remain within the closed valve sleeve when the valve is in the closed position without being crushed. In one embodiment, the recess is substantially round when valve body 22 is in the closed position, and recess 41 has a diameter sized to receive the guide wire selected. The recess may also be sized to receive catheters. While in the closed position, fluid flow from valve distal end 28 through valve sleeve lumen 52 is greatly reduced, if not totally precluded.

Figure 2:
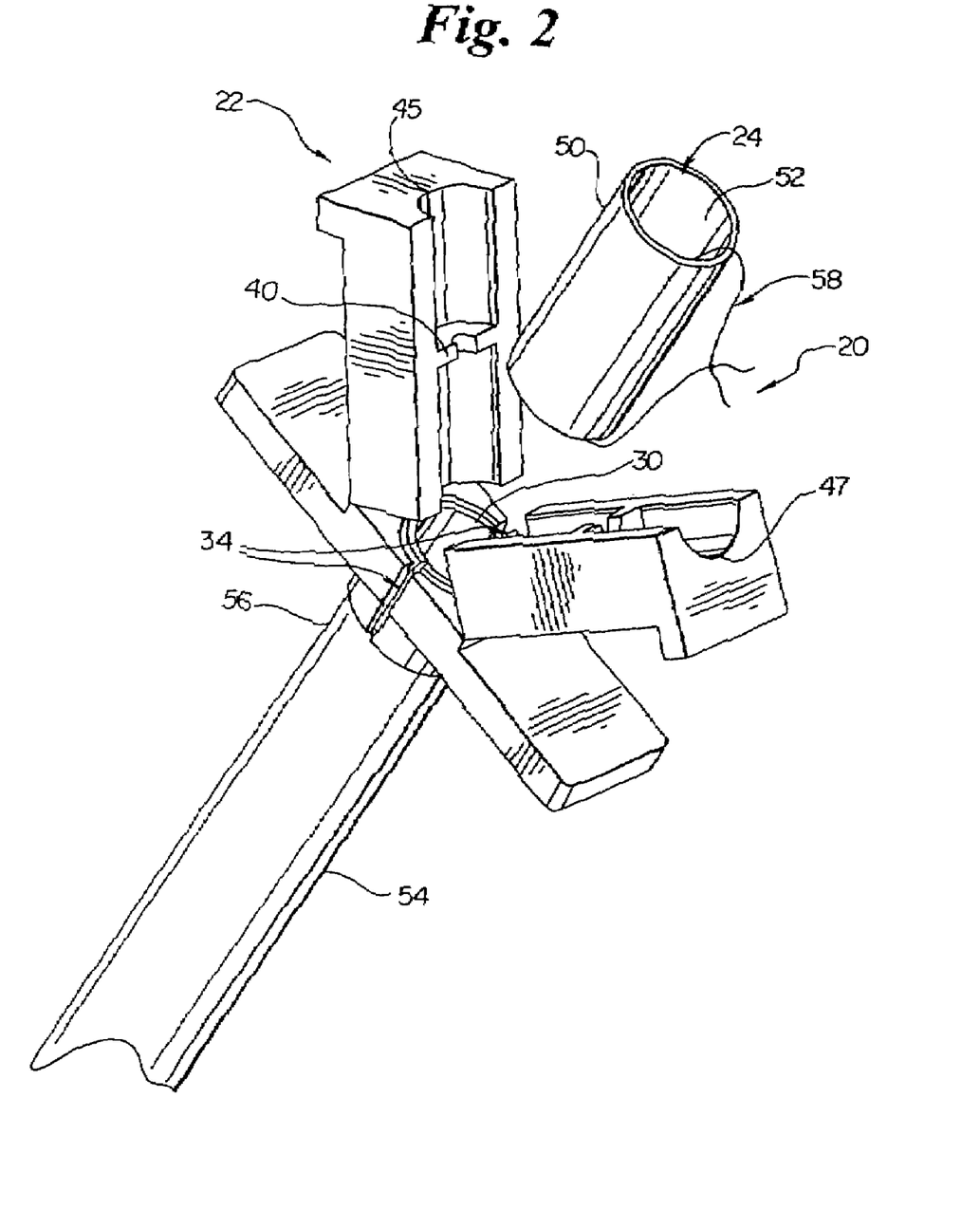
FIG. 2 is an exploded, perspective view of the valve of FIG. 1, coupled to a distal peel-away sheath and having a suture around the proximal valve sleeve.

Referring now to FIG. 2, split valve 20 is further illustrated, having a distal introducer sheath 54 with a proximal region 56 coupled to valve body 22. In the embodiment illustrated, introducer sheath proximal region 56 is received within valve body lumen 30. In a preferred embodiment, introducer sheath 54 is bonded to valve body 22 such that when valve body 22 is split, introducer sheath 54 is split as well. Valve sleeve 24 is illustrated having a suture 58 looped through valve sleeve lumen 52 and tied around the valve sleeve, to allow for easier retrieval in some applications. Suture 58 can be used to lift the sleeve off the catheter shaft to allow a scissors to remove the valve sleeve without cutting the catheter. Suture 58 can also act as a knife to cut valve sleeve 24 for removal from an inserted guide wire or catheter.

Valve body 22 includes a first member proximal aperture 45 and a second member proximal aperture 47. When brought together in a closed position, apertures 45 and 47 form a round entry port for proximal exit of the flexible valve sleeve. The rounded entry port and the flexible valve sleeve contained within are open even when the valve body pinch member 40 has pinched the valve sleeve partially or totally shut. This means that a catheter distal end can be introduced into the valve sleeve portion extending proximally of pinch member 40, even when valve body 22 is in a closed position.

In use, valve body 22 can be closed about inserted valve sleeve 24, thereby pinching valve sleeve 24 substantially closed, and leaving proximal valve sleeve region 50 extending proximally past pinch member 40. In some embodiments, fluid flow through the constricted valve sleeve is totally precluded. In other embodiments, fluid flow is substantially but not totally reduced. Valve body 22 has preferably been securably attached to introducer sheath 54. In one embodiment, valve body 22 is bonded to introducer sheath 54 during manufacture, and delivered to the treating physician as a single piece. In one method of use, a guide wire has previously been introduced into a patient, with a proximal region of the guide wire extending from the patient. The introducer sheath can be inserted over the guide wire with the aid of a dilator and advanced into the vasculature of the patient. As the introducer sheath is advanced sufficiently far, the proximal end of the guide wire should extend past the proximal end of the introducer sheath. In some embodiments, such as the embodiment of FIGS. 1 and 2, a small area of the pinch point has been shaped to include a recess to allow passage of a guide wire. In these embodiments, the valve body can remain closed and the guide wire allowed to pass through the proximal end of the valve. In embodiments not having such a recess, the valve body members can still be closed about the valve sleeve containing the guide wire to form a substantially fluid tight seal.

At some point in a procedure, it will be desirable to introduce a catheter through the introducer sheath. The inside diameter of the introducer sheath and valve sleeve should be selected to be greater than the outside diameter of the catheter distal end and the maximum radial extent of the catheter that is to pass into the sheath or sleeve. The inside diameter of the valve sleeve has preferably been selected to be larger than the catheter distal end outside diameter, but the valve sleeve inside diameter has preferably also been chosen so as to form a reasonably close fit with the outside diameter of the inserted catheter distal end. The catheter distal end can be inserted into valve sleeve proximal region 50 while valve body 22 remains closed. As previously discussed, a catheter distal end can be inserted into flexible valve sleeve proximal region 50 within the proximal port formed by the closure of proximal apertures 45 and 47. In particular, it is not necessary to open valve body 22 to insert the catheter distal end into the valve body. When it is desirable to advance the catheter further distally through valve body 22, the valve body can be opened by pivoting body members 36 and 38 apart, and unconstricting valve sleeve 24. Except for the plugging or occluding effect of the catheter distal end within the valve sleeve, the fluid in the vasculature could flow from the proximal end of valve sleeve 24 once valve body 22 is opened. The pre-placement of the catheter distal end within the valve sleeve proximal region thus has the effect of greatly reducing any leakage of the vessel fluid out of the introducer sheath during the catheter introducing procedure.

After introduction of the catheter through the introducer sheath is complete, or at some other point in a procedure, it may be desirable to remove the introducer sheath, leaving the catheter, and perhaps a guide wire, in place. This can be accomplished by grasping ears or handles 26 and snapping or splitting valve body 22 in two along grooves 34, thereby removing valve body 22 from close proximity to the inserted catheter. As valve body 22 is split, introducer sheath 54 can be split as well, preferably splitting along predefined weakened longitudinal strips such as grooves, indentations, partial depth perforations, or tear strips embedded along the length of the sheath. The introducer sheath can be retracted proximally as it is torn or peeled away from the catheter it surrounds, which can be left in place. In one method of removal, the sheath is pulled in half, with each half pulled away from the opposing half perpendicularly to the remaining catheter.

Figure 2A:
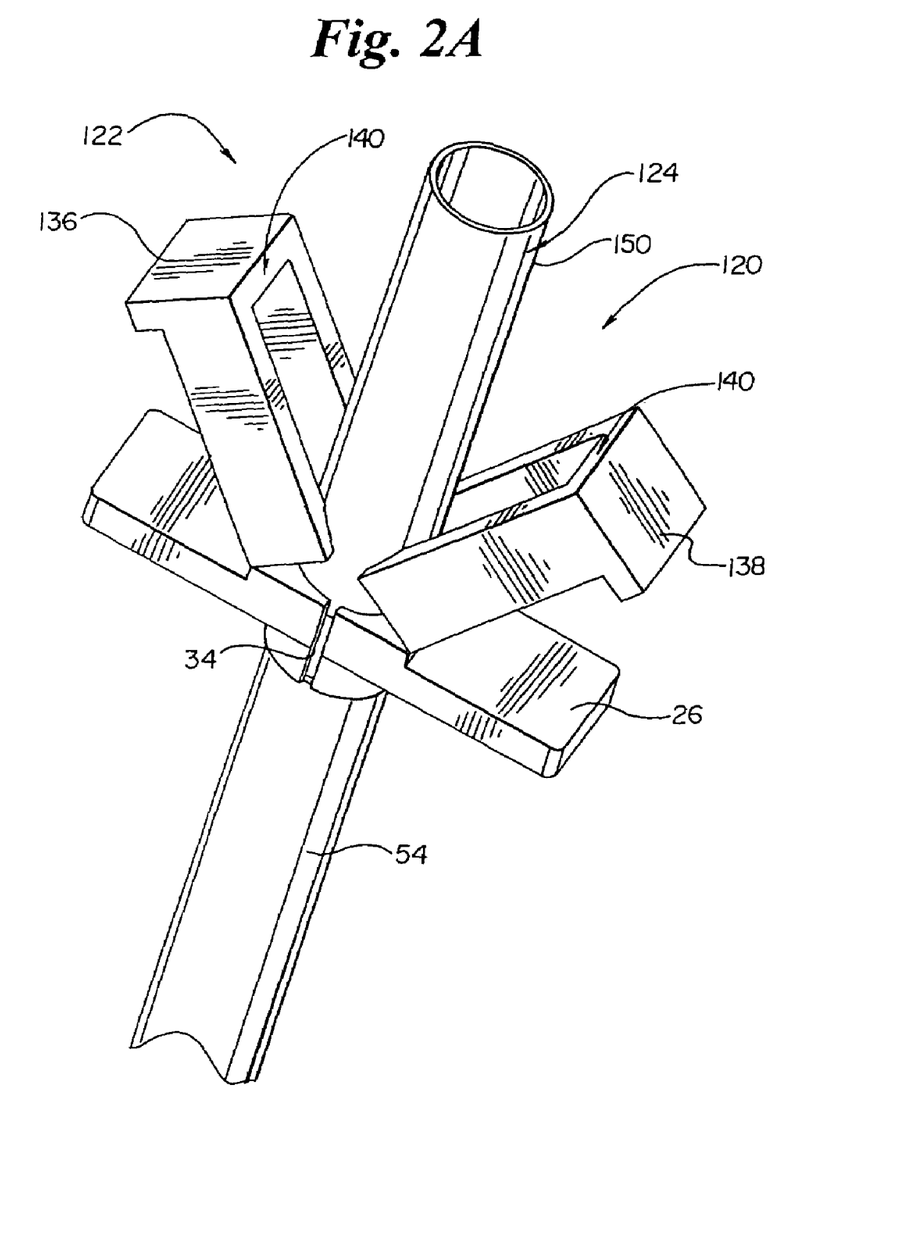
FIG. 2A is a perspective view of a valve similar to the valve of FIG. 1, but having a more proximal pinch point and a longer valve sleeve extending proximally past the pinch point and valve body.

Referring now to FIG. 2A, another introducer sheath assembly 120 is illustrated, having a valve body 122 including a first pivoting body member 136 and an opposing second pivoting body member 138. Valve assembly 120 is similar in some respects to valve assembly 20 in FIGS. 1 and 2, but with valve body 122 having a proximal pinch point or pinch member 140 disposed more proximal than midrange pinch member 40 illustrated in FIG. 1. Valve assembly 120 also includes a valve sleeve 124 having a proximal region 150 which extends past the proximal end of valve body members 136 and 140 when closed. Valve sleeve 124 is longer than valve sleeve 24 illustrated in FIG. 1, to offer a proximal region extending proximally beyond the more proximal pinch point. Valve assembly 120 also allows a catheter to be inserted into valve sleeve 124 before valve body 122 is opened by presenting an already plugged valve sleeve when valve 122 is opened, thereby minimizing blood loss.

Figure 3:
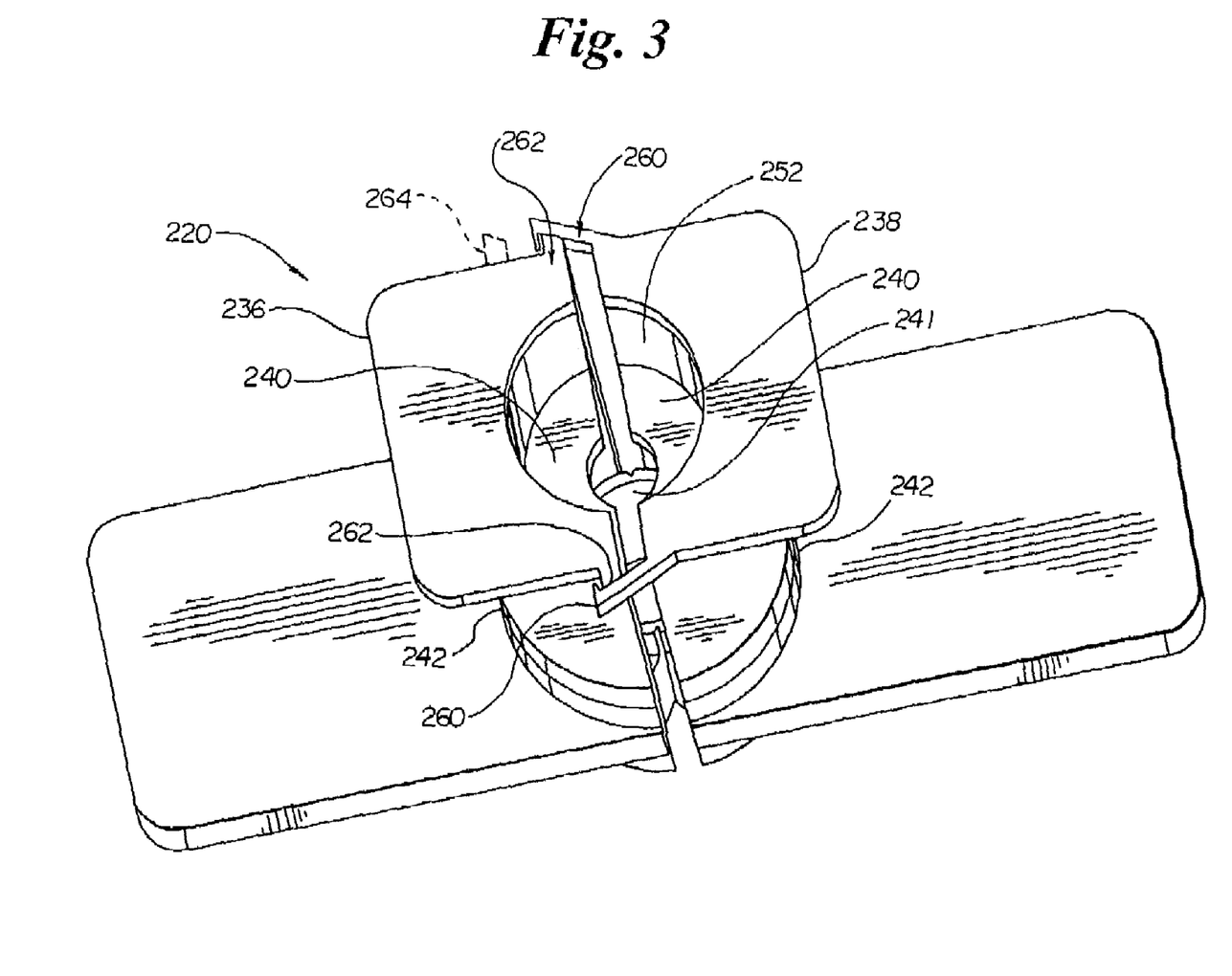
FIG. 3 is a perspective view of a split valve held in a closed position with a latch mechanism and corresponding notches, and including a pinch point having a central lumen therethrough while in the closed position.

Referring now to FIG. 3, another embodiment of the invention is illustrated in valve body 220, having a first body member 236 and a second body member 238 held together with a pair of latches 260 hooked over a pair of notches 262. The flexible valve sleeve (not illustrated in FIG. 3) lies between body members 236 and 238. Valve body 220 has a lumen 252 therethrough, and pinch members 240 have a lumen 241 therethrough formed by a recess in pinch members 240. Pinch member lumen 241 has the advantage of allowing passage of a guide wire through a valve sleeve inserted through valve body 220 when first and second members 236 and 238 are closed. Valve body 220 is also illustrated having an optional notch 264. The additional notch and/or an extra, longer latch can make the valve body closure adjustable. In the embodiment illustrated in FIG. 3, valve body members 236 and 238 are hinged at 242 along a plane extending transversely through valve body lumen 252. The valve body can be split by grasping the handles and breaking the valve body apart.

Figure 4:
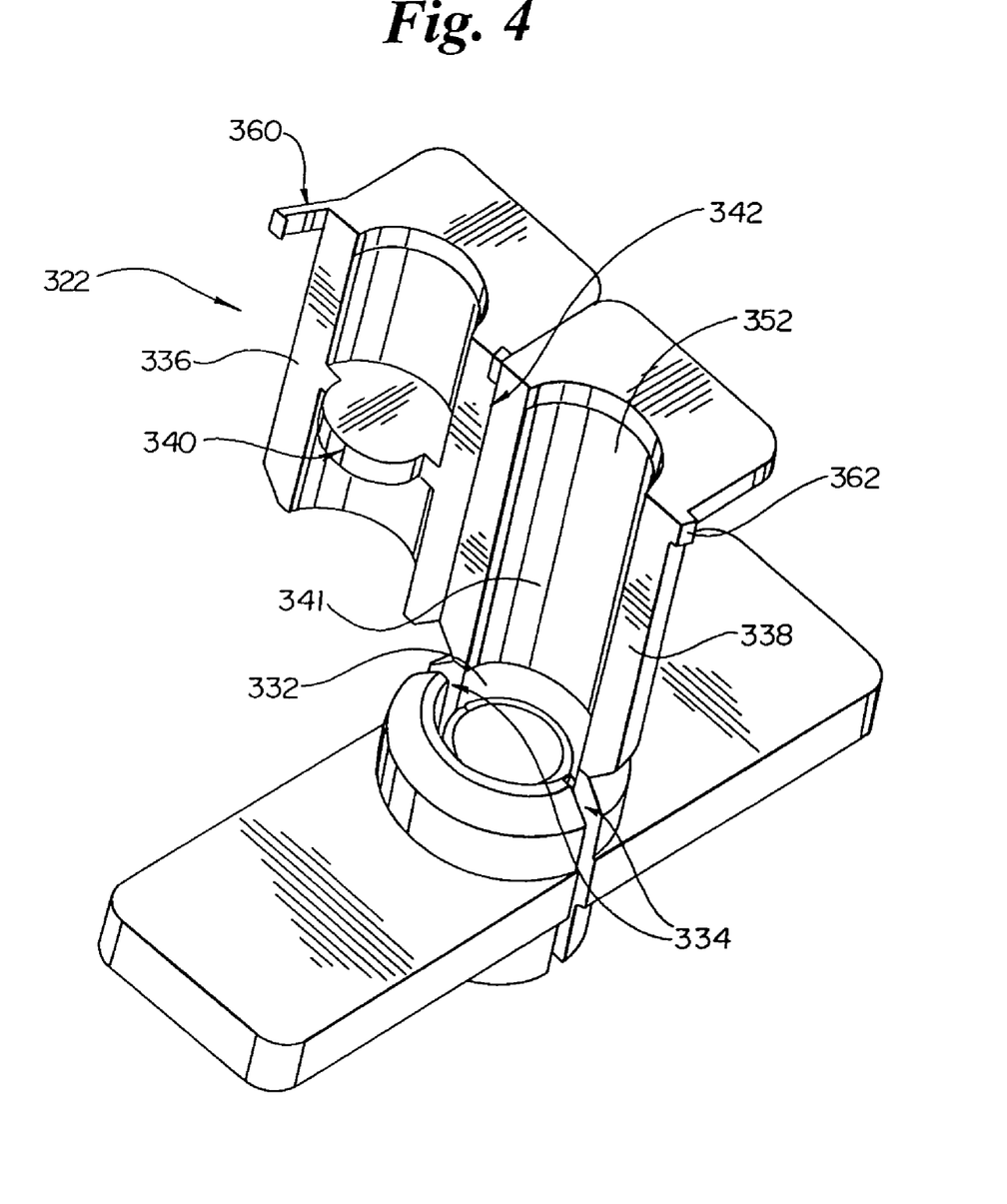
FIG. 4 is a perspective view of a hinged split valve in an open position and having a rounded, convex pinch member on a moveable hinged valve body member to mate to the rounded concave inner wall of the non-movable valve body member.

FIG. 4 illustrates another embodiment of the invention in a valve body 322, having a first, movable body member 336 hingedly attached to a second, stationary body member 338 along a hinge 342 which is parallel to the longitudinal axis of a lumen 352 disposed within valve body 322 when first and second members 336 and 338 are closed. A round, convex pinch member 340 on first member 336 can be adapted to fit closely against a corresponding round, concave interior portion 341 of second member 338. The valve sleeve (not shown) will be compressed between first member 336 and second member 338 by pinch members 340 and 341, greatly constricting the valve sleeve lumen and substantially reducing or totally precluding flow through the valve sleeve lumen. First member 336 and second member 338 are held together when closed by a latch 360 and a corresponding notch 362. FIG. 4 also illustrates a valve seat 332 similar to the valve seat of FIG. 1 and a snap groove 334, showing the weakened area along which preferential breaking will occur when the valve body is snapped.

Figure 5:
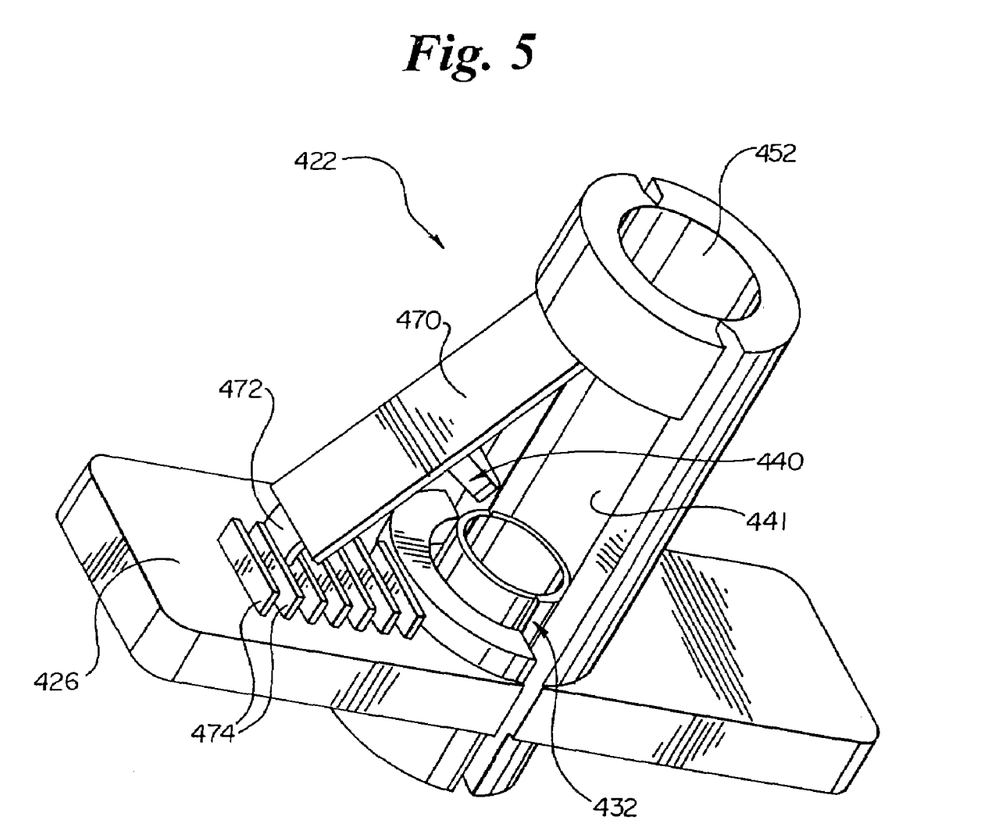
FIG. 5 is a perspective view of a split valve having a pinch point with varying degrees of constriction held in place by a hinged arm having a ratchet securable at multiple notches.

Referring now to FIG. 5, another embodiment of the invention is illustrated in a valve body 422 having a lumen 452 extending therethrough. A valve sleeve (not shown) can be received within the lumen and coupled with a valve sleeve seat 432. Valve body 422 includes a pinch member 440 for compressing a valve sleeve against a concave portion 441 of valve body 422. Pinch member 440 is mounted on a hinged arm 470 which can be secured in position using a ratchet 472 disposed on the end of arm 470 for engaging a series of notches 474 disposed on an ear or handle 426. The ratchet and multiple notches provide a valve body which can close against the inserted valve sleeve in increments. This allows the degree of constriction of the flexible valve sleeve to be controlled incrementally, rather than simply open or shut. The valve sleeve can be opened entirely by lifting arm 470 out of notches 474.

Numerous advantages of the invention covered by this document have been set forth in the foregoing description.

It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A valve for a tubular peel-away sheath having a lumen therethrough comprising:
   a valve body having a lumen therethrough;
   means for preferentially breaking said valve body along a predetermined location in response to applied force, such that said valve body lumen splits open upon breaking;
   means for coupling said valve body to said peel-away sheath for coupling said peel-away sheath lumen to said valve body lumen;
   means for receiving a compressible valve sleeve;
   a compressible valve sleeve having a proximal end, a distal end, and a lumen adapted to receive a distal portion of a medical device; and
   means for compressing said valve sleeve for restricting any fluid flow from said peel-away sheath lumen through said valve and valve sleeve lumen, said proximal end of said compressible valve sleeve extending proximal of said means for compressing said valve sleeve.

2. A valve as recited in claim 1, wherein said valve sleeve includes a free end extending past said means for compressing, and further comprising means for receiving a catheter tip within said valve sleeve lumen free end while said means for compressing is compressing said valve sleeve, such that said valve sleeve lumen is substantially occluded by said inserted catheter tip while said catheter tip is inserted.

3. A breakaway valve for a tubular peel-away sheath, said sheath having an external surface, a lumen, and a proximal end comprising:
   means for reversibly restricting fluid flow from said sheath lumen coupled to said sheath proximal end, wherein said means for reversibly restricting fluid flow includes a compressible valve sleeve and means for compressing said valve sleeve, said valve sleeve having a proximal end and a distal end and a lumen therethrough, the proximal end of said valve sleeve extending proximal of said means for reversibly restricting fluid flow and including means for admitting a catheter distal end into said valve sleeve lumen; and
   means for breaking apart said fluid flow restricting means responsive to applied force.

4. A breakaway valve as recited in claim 3, wherein said means for reversibly restricting flow has an open position for allowing flow therethrough and a closed position for substantially restricting flow, wherein said means for admitting said catheter distal end includes means for admitting said catheter distal end while said means for restricting flow is in said closed position.

5. A breakaway valve as recited in claim 4, wherein said compressible valve sleeve includes a flexible, constrictable tube having a lumen therethrough.

6. A breakaway valve as recited in claim 5, wherein said means for restricting flow is adapted for pinching said flexible tube for constricting said flexible tube lumen.

7. A breakaway valve as recited in claim 6, wherein said means for pinching has at least two portions movable with respect to each other, said two portions having means for accepting and pinching said flexible tube therebetween, said two portions together having an open position and a closed position.

8. A breakaway valve as recited in claim 7, wherein said movable pinching member portions are hingedly coupled together with at least one hinge.

9. A breakaway valve as recited in claim 8, wherein said sheath has a longitudinal axis and said at least one hinge has an axis substantially parallel with said sheath longitudinal axis and said hinge enables movement of said pinching member portions about said hinge longitudinal axis for pinching said flexible tube in said closed position.

10. A breakaway valve as recited in claim 8, wherein, when in said closed position, said pinching members include means for leaving sufficient space in said flexible tube lumen for passage of a guide wire.

11. An introducer sheath assembly for introducing a catheter distally into a human body comprising:
    a tubular, distal introducer sheath having a proximal region and a lumen therethrough, said sheath having at least one longitudinal strip for preferentially tearing said sheath along said strip;
    a tubular, compressible, proximal valve sleeve having a proximal region, a distal region, and a lumen therethrough; and
    a valve body having a lumen therethrough and being sealingly coupled to said introducer sheath proximal region, said valve having at least one weakened region for preferentially splitting said valve into at least two pieces responsive to an applied breaking force, said valve body having a seat for mating to said proximal valve sleeve distal region, said valve body including a pinch member for pinching said flexible valve sleeve and having a closed position for constricting fluid flow through said valve sleeve and an open position for admitting a catheter inserted through said valve sleeve; wherein said proximal region of said proximal valve sleeve extends proximal of said pinch member and is adapted to receive a medical device.

12. An introducer sheath assembly as recited in claim 11, wherein said flexible valve sleeve includes a free portion proximal of said pinch member for admitting said catheter into said sleeve free portion while said pinch member is in said closed position.

13. An introducer sheath assembly as recited in claim 11, wherein said valve body pinch member includes a recess therein for allowing passage of a guide wire through said pinch member while said pinch member is in said closed position.

14. A breakaway valve body for restricting flow from a peel-away introducer sheath having a proximal region and a lumen therethrough comprising:
    a breakaway distal portion having a lumen therethrough for receiving said introducer sheath proximal region; and
    a proximal portion including two opposed valve body members, at least one of which is movable relative to the other and having concave surfaces therebetween for receiving a flexible valve sleeve therebetween, said valve body opposed members having an open position and a closed position, wherein said valve body members move apart relative to each other to reach said open position and said valve body opposed members move together relative to each other to reach said closed position, wherein said flexible sleeve has a lumen therethrough adapted to receive a medical device, said flexible sleeve having a proximal end, and a distal end, said proximal end extending proximal of said body members, said sleeve being compressible, and said sleeve and sleeve lumen are constricted between said body members in said closed position, such that fluid flow through said sleeve is substantially restricted in said closed position.

15. A breakaway valve body as recited in claim 14, wherein said valve body members are pivotally mounted to each other along at least one hinge oriented substantially parallel to said valve body lumen longitudinal axis.

* * * * *